(12) United States Patent
Wilson

(10) Patent No.: US 8,400,172 B2
(45) Date of Patent: Mar. 19, 2013

(54) DEGRADATION SENSOR

(75) Inventor: Alan Richard Wilson, Glen Iris (AU)

(73) Assignee: The Commonwealth of Australia, Department of Defense (AU)

( * ) Notice: Subject to any disclaimer, the term of this patent is extended or adjusted under 35 U.S.C. 154(b) by 294 days.

(21) Appl. No.: 12/863,401

(22) PCT Filed: Jan. 28, 2009

(86) PCT No.: PCT/AU2009/000083
§ 371 (c)(1),
(2), (4) Date: Jul. 29, 2010

(87) PCT Pub. No.: WO2009/097645
PCT Pub. Date: Aug. 13, 2009

(65) Prior Publication Data
US 2011/0050259 A1   Mar. 3, 2011

(30) Foreign Application Priority Data

Feb. 5, 2008  (AU) ................................ 2008900518

(51) Int. Cl.
*G01R 27/08*  (2006.01)

(52) U.S. Cl. .......................... 324/700; 324/691; 324/693
(58) Field of Classification Search ................. 324/693, 324/700, 707, 713, 691
See application file for complete search history.

(56) References Cited

U.S. PATENT DOCUMENTS 5,528,155 A * 6/1996 King et al. ..................... 324/713
5,895,843 A   4/1999 Taylor et al.
6,383,451 B1  5/2002 Kim et al.

* cited by examiner

*Primary Examiner* — Vincent Q Nguyen
(74) *Attorney, Agent, or Firm* — Young Basile Hanlon & MacFarlane, PC; Denise M. Glassmeyer

(57) ABSTRACT

A sensor for monitoring a structure or material. The sensor has a continuous elongate conducting member embedded in an insulating material and a conductivity or resistance meter. The insulating material has one or more gaps that expose the conducting member without allowing direct contact between the insulating material and the structure or material when the sensor is placed against the structure or material. The meter is arranged to monitor conductivity or resistance between the conducting member and the structure or material being monitored, and/or between two regions of the conducting member.

23 Claims, 4 Drawing Sheets

DEGRADATION SENSOR

RELATED APPLICATION

This application is based on and claims the benefit of the filing date of AU application no. 2008900518 filed 5 Feb. 2008, the content of which as filed is incorporated herein by reference in its entirety.

FIELD OF THE INVENTION

The present invention relates to a sensor for monitoring a structure or material, to detect the effects of possible corrosion or other deterioration of structures (including buildings, vehicles, vessels or parts thereof) and materials.

BACKGROUND OF THE INVENTION

One existing method for detecting corrosion (disclosed in U.S. Pat. No. 6,805,788) employs electrochemical impedance spectroscopy. The conductivity of the monitored substrate is measured by locating a probe with a solid polymer electrolyte membrane that houses an electrode in contact with the surface of the substrate. Perturbations in an AC current or voltage across the monitored surface and the electrode are used to determine the impedance of the substrate. However, the probe monitors for differences—from one area of a monitored surface to another—in surface conductivity as an indication of corrosion activity, and requires access by the probe to the region of concern. Also, the probe appears unlikely to be sensitive to water ingress; instead it will only show actual corrosion.

WO 87/04525 discloses a corrosion sensor that compares the resistivity of a reference element (not exposed to corrosion) and that of a test element coating the reference element and exposed to corrosion. However, this approach relies on the relative resistivity of the reference and test elements, so always requires the use of the two elements.

WO 00/46593 discloses a micro-electronic bond degradation sensor with a sensor substrate having sensor circuitry and a sensor stud and a power stud extending therefrom. The sensor circuitry includes a voltage-to-current amplifier with an input coupled to the sensor stud and an output coupled to the power stud, and operable to convert a voltage signal occurring along the sensor stud to a current signal output along the power stud.

SUMMARY OF THE INVENTION

In one broad aspect, therefore, the present invention provides a sensor for monitoring a structure or material, comprising:
- an elongate conducting member; and
- an insulating material within which is embedded the conducting material;
- wherein the insulating material has one or more gaps located along the insulating material that expose the conducting member without allowing direct contact between the insulating material and the structure or material when the sensor is placed against the structure or material.

Corrosion of a structure or material can be monitored by fastening the sensor to the structure or material such that the sensor is located against the structure, and monitoring conductivity or resistance between the structure and conducting member. Furthermore, corrosion of the structure or material may be accompanied by corrosion of the conducting member, depending on the material from which the conducting member is made, so changes in the conductivity or resistance may be indicative of corrosion (or other deterioration) in the structure or material. Consequently, corrosion of a structure or material can in some cases be monitored by monitoring the conductivity or resistance of the conducting member between two regions of the conducting member. This may be done as an alternative to—or to supplement—the monitoring of conductivity or resistance between the structure and conducting member.

Additionally, the sensor may be embedded in a coating—such as an adhesive, sealant or paint—that has been applied to the structure or material. For example, the sensor may be located between a primer and an outer coat of paint, or within sealant or adhesive located on or between two portions of a structure. In such cases, the ingress of water or some other corrosive into the coating will commonly lead to increased conductivity between the structure or material and the conducting member.

Moreover, the conducting member may also corrode, ultimately leading to a loss of conductivity of the conducting member over its length. The corrosion of the conducting member—whose rate may be advantageously controlled by selection of the material of the conducting member, particularly in view of the nature of the monitored site—provides a useful alternative or additional measure of the corrosion of the monitored structure or material.

When the sensor is embedded in a coating, such as an adhesive, the electrical properties of the coating may by monitored between the gap or gaps and another conducting material in the medium.

For example, if the sensor is included in an adhesive joint that includes a metallic adherend then the conductivity between the exposed conducting member of the sensor and the adherend can be measured. This conductivity will be affected by the presence of ions between the conducting member of the sensor and the metallic adherend, such ions being generated by corrosion or other degradation processes that may be occurring or have occurred. Alternatively, if the adhesive (or paint) has been applied to a non-conducting structure or material, another wire—uninsulated—or a further sensor may be located near the sensor to provide the other conductor and hence a conducting path.

The conducting member typically comprises a wire or metallic ribbon, and may comprise a plurality of conducting elements (such as a plurality of wire or metallic ribbons).

The conducting member may comprise a plurality of conducting elements of dissimilar materials, allowing the use of electrochemical potentials between conducting elements as a monitoring signal. In such embodiments, the sensor may include a meter arranged to detect a potential difference between a pair of the conducting elements. The meter may be arranged to output a signal in response to a predefined value of the potential difference or a predefined change in the potential difference. The signal may be, for example, indicative of the potential difference, may be indicative of the change in the potential difference or may be an alarm signal.

The gaps in the insulating material, particularly if the insulating material comprises a plurality of conducting elements, may be filled (such as through a recoating process) with a material or materials sensitive to chemical or physical stimuli, such as light, temperature or chemical species, thus making the sensor sensitive to these stimuli. In such embodiments, changes may be monitored in conductivity or resistance between the conducting member at the location of such a gap and another conductor. The other conductor may be another sensor, but need not be. Alternatively, changes may be monitored in conductivity or resistance between two sensors with gaps filled with and connected by such sensitive material; that is, the measurement of conductivity or resistance is made via the sensitive material. This might be done by embedding two sensors in the sensitive material, and measuring the conductivity or resistance between the two sensors.

The insulating material may comprise any material that can coat or partially coat the conducting member to form an insulating layer (even if porous to some degree) that will hold the conducting member away from the monitored structure or material (and hold respective conducting elements apart in embodiments in which the conducting member comprises a plurality of conducting elements).

In one embodiment, therefore, the insulating material comprises polyurethane and in another embodiment the insulating material comprises nylon. However, other insulating materials are'clearly possible, including—for example—an oxide coating formed on the conducting member.

The gap or gaps may comprise, for example, apertures in the insulating material or annular breaks in the insulating material. It will be appreciated that—as the gap or gaps do not allow direct contact between the insulating material and the structure or material—the size of the gap or gaps will vary according to factors such as the thickness of the insulating material and the roughness of surface or surfaces with which the sensor is in contact.

The sensor may include a conductivity or resistance meter, for monitoring conductivity or resistance between the conducting member and a structure or material being monitored for corrosion or deterioration with the sensor, or between two regions of the conducting member, or both. If between two regions of the conducting member, the two locations may comprise, for example, two ends of the conducting member, an end of the conducting member and a location on the conducting member remote from the two ends of conducting member, or two locations on the conducting member remote from the two ends of the conducting member and separate from each other. In embodiments where the conducting member comprises a plurality of conducting elements, the two regions of the conducting member may comprise a first region that is on a first conducting element and a second region that is on a second conducting element.

The meter may be configured to issue an alarm or other signal when the conductivity decreases significantly or the resistance increases significantly.

The invention also provides a method for monitoring a structure or material, comprising:
 placing the sensor described above against the structure or material; and
 monitoring conductivity or resistance between the structure or material and the conducting member, or between two regions of the conducting member, or both between the structure or material and the conducting member and between two regions of the conducting member.

The meter may be configured to issue an alarm or other signal when the conductivity decreases significantly or the resistance increases significantly.

The method may include adhering the sensor to the structure or material, such as with an adhesive material, such as glue, a sealant or paint. (The paint may be that used to paint the structure or material, exploited to additionally adhere the sensor to the structure or material.) In other embodiments, however, the method includes mechanically fastening the sensor to the structure or material.

The method may include embedding the sensor in a coating, such as an adhesive, sealant or paint applied to the structure or material.

The method may include employing time-of-flight measurements or rise time measurements to locate a location of corrosion or deterioration.

The method may include employing frequency dependent measurements to measure a complex impedance of the sensor.

According to another broad aspect, the invention provides a structure or material provided with a sensor as described above.

BRIEF DESCRIPTION OF THE DRAWING

In order that the invention may be more clearly ascertained, embodiments will now be described, by way of example, with reference to the accompanying drawings, in which.

DETAILED DESCRIPTION

Figure 1:
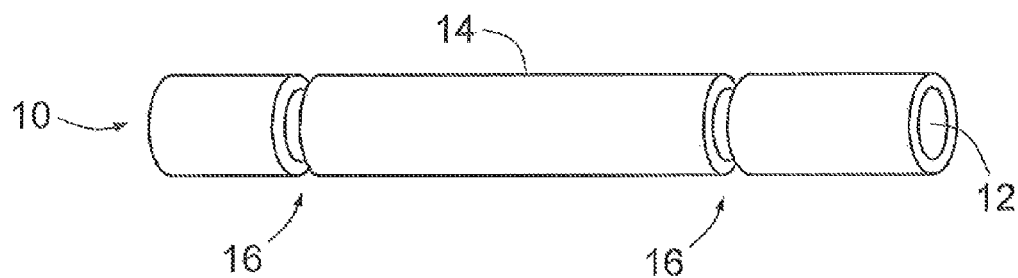
FIG. 1 is a schematic view of a wire sensor according to an embodiment of the present invention.

A sensor for detecting corrosion or other deterioration in typically metal surfaces, according to an embodiment of the present invention, is shown generally at 10 in FIG. 1. Sensor 10—formed from insulated wire (and hence also referred to as a 'wire sensor')—comprises a thin wire 12 of 25 µm to 200 µm diameter and, covering the wire, a thin insulating material 14, such as polyurethane or nylon, that is a few microns in thickness. Sensor 10 also has periodically spaced notches 16 where wire 12 is exposed, that is, there is no overlaying insulating material 14. Notches 16 are spaced 100 µm apart, though it will be appreciated that this spacing can be smaller or greater, including of the order of millimetres or more. Each notch 16 has a width—along the length of sensor 10—of 5 to 30 µm; in many applications a width at the smaller end of this range is preferable.

As will also be appreciated by those skilled in the art, sensor 10 may be of essentially any desired length, and may have essentially any desired number of notches 16. Further, notches 16, though located periodically along sensor 10, may in other embodiments be spaced by varying amounts or grouped in clusters of notches. Also, although wire 12 is of circular cross section, in other embodiments (including those described below), wire 12 may assume other forms, including a ribbon or strap of conductor.

Figure 2:
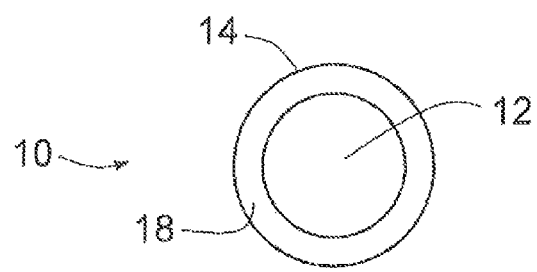
FIG. 2 is a cross sectional view of the wire sensor of FIG. 1.

FIG. 2 is a cross sectional view of sensor 10 at the location of the centre of a notch 16. In this view, it will be noted, the exposed face 18 of insulating material 14 is behind the plane of the exposed portion of wire 12 by half the width of notch 16.

Figure 3:
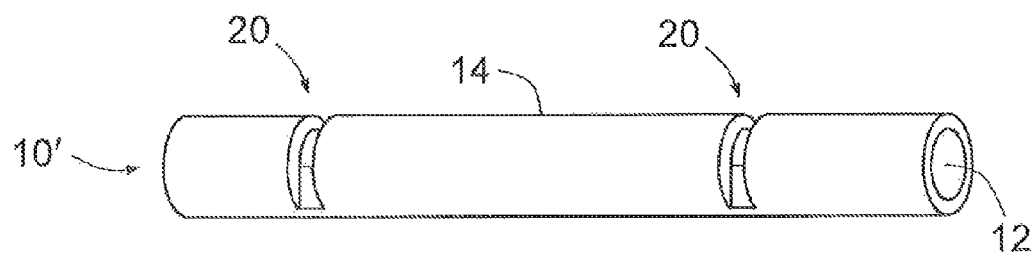
FIG. 3 is a schematic view of a wire sensor according to another embodiment of the present invention.
Figure 4:
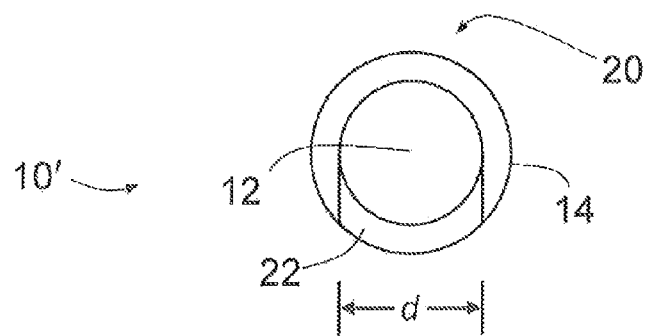
FIG. 4 is a cross sectional view of the wire sensor of FIG. 3.

FIG. 3 is a schematic view of a wire sensor 10' according to another embodiment of the present invention. Sensor 10' is identical in most respects with sensor 10 of FIG. 1, and like reference numerals have been used to identify like features. However, whereas each of notches 16 of sensor 10 of FIG. 1 corresponds to the removal of a complete annular piece of insulating material 14, each of notches 20 of sensor 10' corresponds to the removal of most—but not all—of such an annular piece of insulating material 14. FIG. 4 is a cross sectional view of sensor 10' of FIG. 3, through a notch 20. It may be seen that a small portion 22 of insulating material 14, equal in width to the diameter d of wire 12, remains in each notch 20. This results from the use of a laser beam (projected from above in the view of FIGS. 3 and 4) to ablate insulating material 14 and form notches 20; the small remaining portions 22 of insulating material 14 are left in place, being protected from the laser beam by wire 12.

Figure 5:
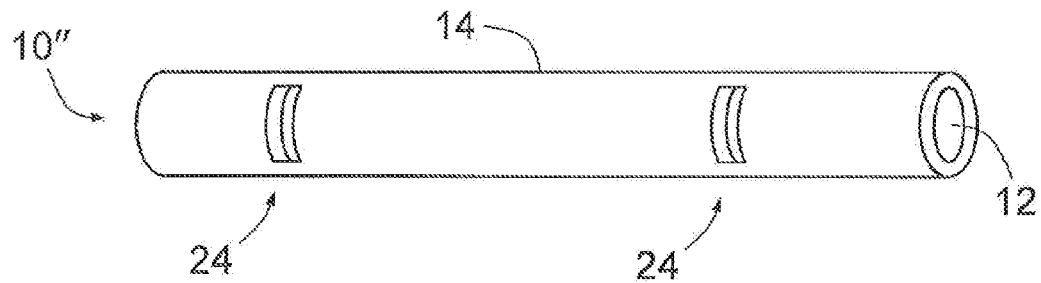
FIG. 5 is a schematic view of a wire sensor according to still another embodiment of the present invention.
Figure 6:
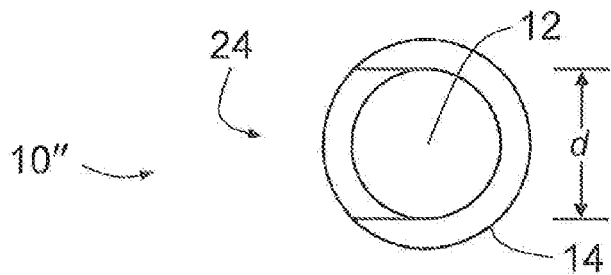
FIG. 6 is a cross sectional view of the wire sensor of FIG. 5.

FIG. 5 is a schematic view of a wire sensor 10" according to another embodiment of the present invention. Sensor 10" is also identical in most respects with sensor 10 of FIG. 1, and like reference numerals have been used to identify like features. However, whereas each of notches 16 of sensor 10 of FIG. 1 corresponds to the removal of a complete annular piece of insulating material 14, each of notches 24 of sensor 10" corresponds to the removal of only a segment of insulating material 14. FIG. 6 is a cross sectional view of sensor 10" of FIG. 5, through a notch 24, from which it is evident that only a segment of insulating material 14, equal in width to the diameter d of wire 12, is removed to form each notch 24 (such as by laser ablation with a laser beam projected from the left in the view of FIG. 6).

Sensors 10, 10' and 10" are manufactured from wire by removing insulating material 14, such as with a laser, from the original wire at the desired periodic (or other) spacing and with the desired width. Insulating material 14 is removed using a laser system set up to ablate the insulating material but have little or no effect on wire 12. For example, an AVIA frequency tripled ND:YAG laser operated at the appropriate fluence can produce 6 μm wide cuts in a 3 μm thick polyurethane insulating material with little impact on an underlying 50 μm thick Al 2024 alloy wire. Alternatively an excimer laser may be used to remove insulating material 14, also with little effect on wire 12.

Figure 7A:
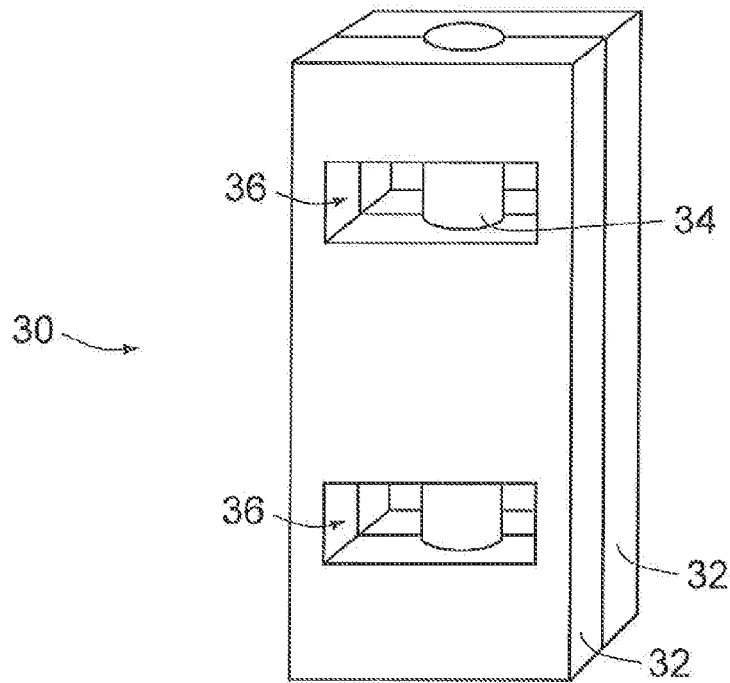
FIG. 7A is a schematic view of a wire sensor according to a further embodiment of the present invention.
Figure 7B:
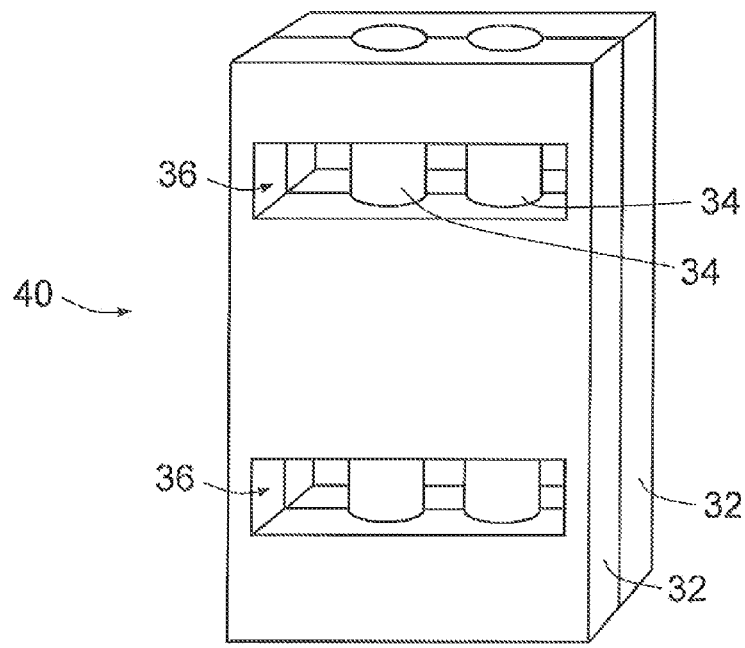
FIG. 7B is a schematic view of a variation of the wire sensor of FIG. 7A.

Alternatively, thin metal wire can be coated or laminated as required to provide the same characteristics. FIGS. 7A and 7B are schematic views of wire sensors 30, 40 according to still further embodiments of the present invention, in which insulating material 32 is laminated around wire 34. Sensors 30, 40 have periodic slots 36 where insulating material 32 has been removed to expose wire 34. Sensor 40 differs from sensor 30 only in that sensor 40 has two wires 34 laminated between insulating material 32, arranged to be in parallel with each other but separated so that there is no direct electrical contact between them. The laminated insulating material 32 can be precut to include slots 36 (either on one or both sides) or can be excised after lamination to expose wire 34. Lamination would typically be employed in applications in which a thick layer of insulating material is required.

The width of notches 16 and slots 36, and the thickness of insulating material 14, 32, can be varied as desired, provided that, when a sensor 10, 10', 10", 30, 40 is placed against a conducting metal surface to be monitored for corrosion under moderate pressure, wire 12 will not make electrical contact with the metal surface. In use, sensor 10, 10', 10", 30, 40 is placed on the conducting metal surface that is to be monitored for corrosion. Sensor 10, 10', 10", 30, 40 is held against the metal surface by being placed, for example, under paint, or surrounded by a sealant or adhesive. Sensor 10, 10', 10", 30, 40 is not in electrical contact with the surface, even if insulating material 14, 32 is in physical contact with the metal surface, as conducting wire 12 is recessed within notches 16 or slots 32. When corrosion occurs the conductivity between wire 12 and the conducting metal surface changes, typically from essentially zero to some measurable value, as the metal surface or the coating (i.e. the paint, sealant or adhesive) deteriorates. Thus, corrosion is assessed by measuring—periodically or continuously—the conductivity between wire 12 and the metal surface (such as with a sensitive ohmmeter).

In addition, in cases of pronounced corrosion, wire 12 may itself corrode to the point that wire 12 is effectively broken and sensor 10, 10', 10", 30, 40 becomes an open circuit. Thus, conductivity is also measured, according to this embodiment, either between the ends of wire 12 or, for greater localization, between one or more pairs of notches 16 or slots 32.

Thus, as described above, sensor 10, 10', 10", 30, 40 is in use located close to a conductive surface so that, if a conductive environment forms between the wire and the surface a change in conductivity between the wire and surface will be detected. However, how this is done may depend on the application. The following illustrative applications are described with reference to sensor 10, but in each case sensors 10', 30, 40 (and variations thereof) are also suitable.

Figure 8:
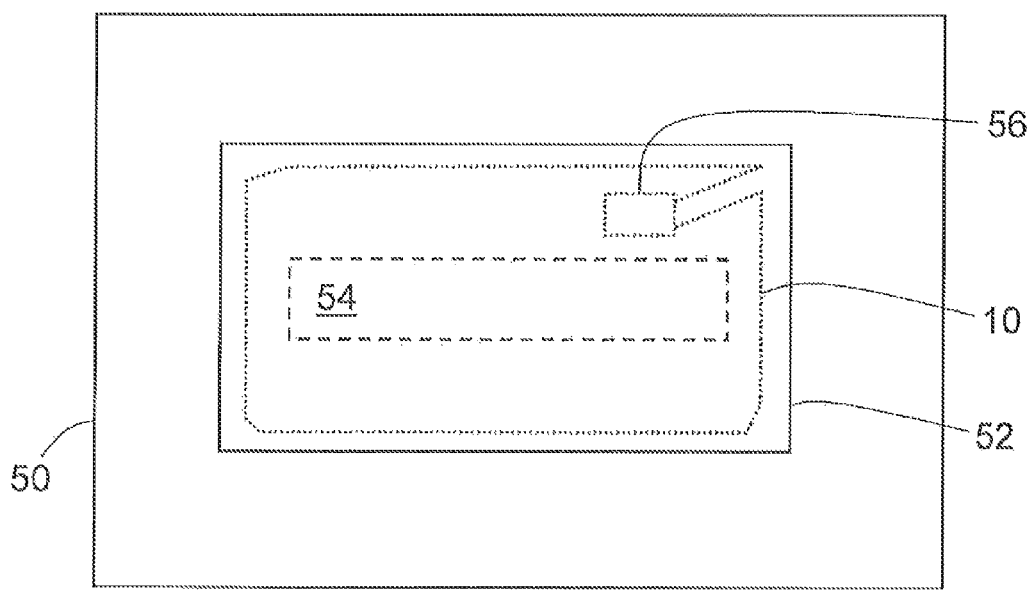
FIG. 8 is a schematic view of a metal plate bonded to metal patch, bonded together with an adhesive and monitored with the wire sensor of FIG. 1.

For example, one application involves adhesive bond monitoring. In this application sensor 10 is placed within an adhesive bond line, such as between two metal plates. FIG. 8 is a schematic view of a metal plate 50 and a metal patch 52, bonded together with an adhesive (not shown) so that metal patch 52 patches a crack or hole 54 in metal plate 50. Sensor 10 is located between metal plate 50 and metal patch 52, within the adhesive and near the edge of metal patch 52 (as the edge is most likely to fail owing to environmental degradation). If there is a crack in the inside of metal patch 52 that is exposed to the external environment, another sensor 10 may be located run around this region too. For thick bonds, significantly greater than the width of sensor 10, two sensors 10 may be employed, one on the top of the adhesive and one on the bottom.

Sensor 10 is located by laying it over or under the adhesive. If significant pressure is used in the bonding process it becomes important to correctly fix sensor 10 in position securely, so that it is not displaced by any movement of the adhesive as it is forced out of the joint. For example, thermoset aeronautical adhesives contain a scrim layer that determines the thickness of the final bond. Sensor 10 of the present embodiment could either be directly incorporated into the scrim or be stitched through the scrim to ensure that it is held in place during, for example, a high pressure curing process.

Sensor 10 is terminated—at both its ends—at sensor electronics 56. Sensor electronics 56 measure the conductivity of wire 12 of sensor 10 (and hence of sensor 10 itself), and optionally outputs a signal should any significant difference in that conductivity be detected. Sensor electronics 56 may be powered by any suitable mechanism, including inductive coupling.

Optionally, sensor electronics 56 may be arranged also to monitor conductivity between metal plate 50 and/or metal patch 52 and wire 12 of sensor 10, by electrically coupling sensor electronics 56 to metal plate 50 and/or metal patch 52. Also, it will be appreciated that sensor electronics 56 need not form a part of the illustrated system but be introduced only when patch integrity is to be checked.

Figure 9:
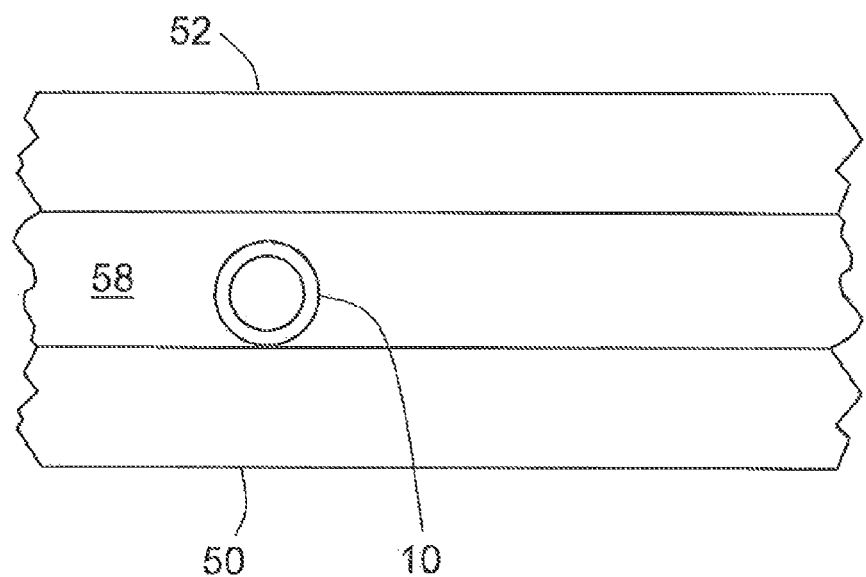
FIG. 9 is a cross sectional view of the arrangement of FIG. 8.

FIG. 9 is a cross sectional view of the arrangement of FIG. 8, including metal plate 50, metal patch 52, adhesive layer 58 (between and adhering metal plate 50 and metal patch 52) and sensor 10 located within adhesive layer 58. Sensor 10 is removed from metal patch 52 by adhesive layer 58, but is in contact with metal plate 50 (though wire 12 of sensor 10 is denied direct contact with metal plate 50 by insulating material 14). Thus, deterioration of the adhesive layer 58 or of the bond between metal plate 50 and metal patch 52 must occur if any significant change in the conductivity of wire 12 of sensor 10 is to be observed.

In another application, sensor 10 is used to monitor dry joints and joints with sealants. Such applications are similar to the use of sensor 10 with adhesive bonds. A pair of sensors 10 are located above and below the sealant in the joint prior to the joint being tightened together. Bolts or rivets should be located prior to placement of sensor 10 to help locate sensor 10 during the joining process. The required electronics for sensors 10 may be located in the joint (if there was enough space) or in a sealed area adjacent to the joint. If the joint has a flat polymer sealant strip then sensors 10 may be fabricated into this strip.

Figure 10:
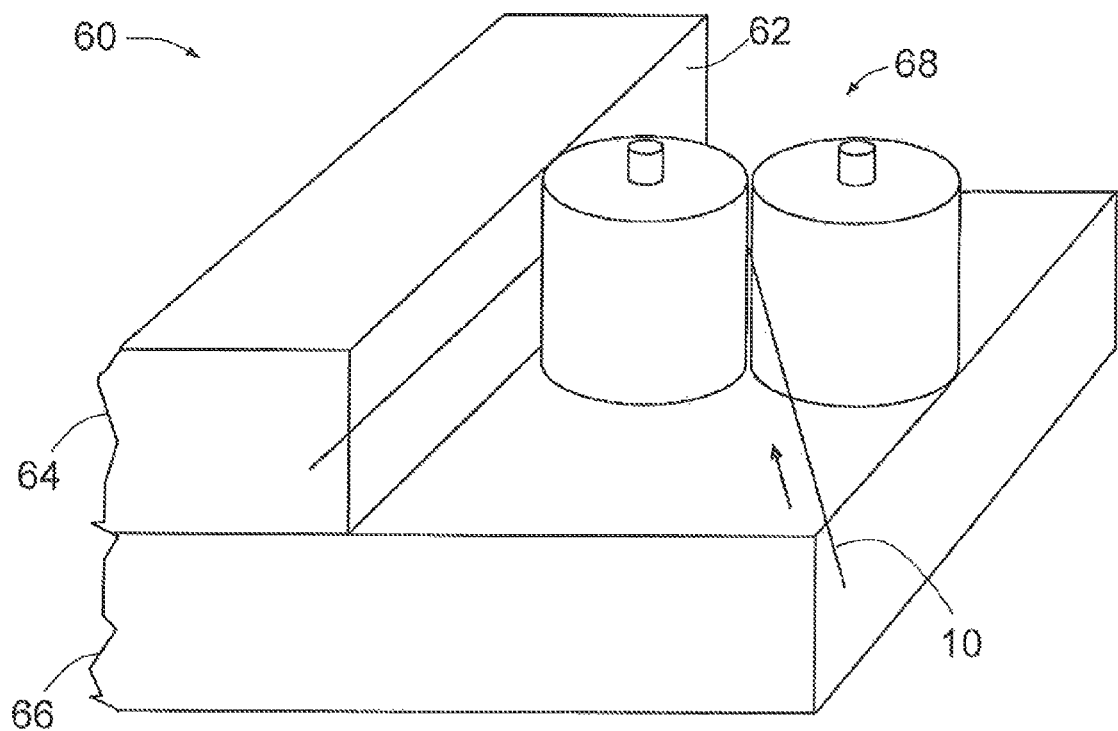
FIG. 10 is a schematic view of the application of the wire sensor of FIG. 1 with paint to the end of a thick metal plate joined to another plate.

In still another application, sensor 10 is used to monitor the condition of sealants and paints. In this application, sensor 10 is typically located in position either prior to or during the sealing/painting process. For example, FIG. 10 is a schematic view 60 of the application of a sensor 10 to the end 62 of a thick metal plate 64 joined to another plate 66. Sensor 10 is laid along end 62 of thick plate 64 with a paint roller 68 that simultaneously applies paint and sensor 10, the paint holding sensor 10 in place. This geometry would be particularly important for aluminium alloys, as exfoliation corrosion, which initiates at the ends of plates, is a particular concern with such materials. Location of sensor 10 on the end 62 of the plate 64 would give early warning of this form of corrosion.

In other applications, sensor 10 is used with non-conductive surfaces. In such applications, where conductivity between surface and sensor 10 will not change appreciably even if wire 12 comes into contact with the surface, sensor 10 can still be used: sensor 10 is installed as a loop and a change in conductivity of wire 12—or indeed of complete loss of conductivity between the ends of wire 12 (and hence the creation of an open circuit)—are indicative of ingress of environmental effects.

In certain applications, a sensor according to the present invention but with a plurality of wires may be more appropriate. One example of such a sensor comprises two (or more) thin wires or strips of an electrically conducting material, each covered by a thin insulating material, are lightly twisted together. The insulating material is removed periodically along the two wires so that the regions with insulation removed are close together. Another example comprises essentially sensor 40 of FIG. 7B, and comprises two (or more) thin wires or straps laminated in non-conductive material with the insulating material removed in thin strips—to form slots in which the wires are exposed—periodically along the two wires.

In such sensors with a plurality of wires, the wires do not have to be of the same material though they will commonly be so.

Such sensors can be used in similar applications to those of the single wire sensors. In addition, they can be used when there is no conductive surface; conductivity between the two wires is then used to monitor for corrosion. Again, the wires may themselves be attacked by the environment, leading potentially to an open circuit. However, with two wires the onset of this attack may be detected, rather than merely the ultimate open circuit. Also, the condition of any material between the conducting members can be monitored if its properties change as it is degraded by the environment.

Wires constructed of different materials can be monitored for electrochemical current and/or voltage developed in the presence of the environment, forming the basis of distributed electrochemical sensors. Such an electrochemical sensor according to the present invention could comprise three thin wires if a reference electrode is required, though two wires are sufficient if it is only desired to detect a potential generated by two dissimilar metals and some chemical agent that has intruded into the structure or material being monitored, or is a by-product of the degradation process; the sensor would otherwise be fabricated in the same way as a single or dual wire sensor.

As described above, the simplest way to interrogate sensor 10 is by monitoring its conductivity for an open circuit condition. In addition, the conductivity between the wire or wires of the sensor and a metal surface may be monitored, as may the conductivity between different wires in a sensor with a plurality of wires.

Other more complex techniques employ time-of-flight measurements or rise time measurements to locate the point on the wire where the conductivity has reduced (i.e. where corrosion has occurred). Dissimilar plural wire sensors can also be monitored for generated voltage or current due to the presence of an environment.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

Further, any reference herein to prior art is not intended to imply that such prior art forms or formed a part of the common general knowledge in Australia or any other country.

The invention claimed is:

1. A sensor for monitoring a structure or material, comprising:
    a continuous elongate conducting member;
    an insulating material within which is embedded said conducting member; and
    a conductivity or resistance meter;
    wherein said insulating material has one or more gaps located along said insulating material that expose said conducting member without allowing direct contact between said insulating material and said structure or material when said sensor is placed against said structure or material, and the meter is arranged to monitor conductivity or resistance between the conducting member and the structure or material, or between two regions of the conducting member.

2. A sensor as claimed in claim 1, wherein said conducting member comprises a wire or metallic ribbon.

3. A sensor as claimed in claim 1, wherein said conducting member comprises a plurality of conducting elements.

4. A sensor as claimed in claim 1, wherein said gaps in said insulating material are filled with a material or materials sensitive to chemical or physical stimuli.

5. A sensor as claimed in claim 1, wherein said insulating material comprises polyurethane or nylon.

6. A sensor as claimed in claim 1, wherein said gap or gaps comprise apertures in said insulating material or annular breaks in said insulating material.

7. A sensor as claimed in claim 1, wherein the meter is arranged to monitor conductivity or resistance both between said conducting member and said structure or material and between two regions of said conducting member.

8. A sensor as claimed in claim 1, wherein said meter is configured to issue an alarm or other signal when said conductivity decreases significantly or said resistance increases significantly.

9. A sensor as claimed in claim 1, wherein said conducting member comprises a plurality of conducting elements of dissimilar materials.

10. A structure or material provided with a sensor as claimed in claim 1.

11. A sensor as claimed in claim 1, wherein the insulating material comprises an oxide coating formed on the conducting member.

12. A sensor for monitoring a structure or material, a comprising:
an elongate conducting member comprising a plurality of conducting elements of dissimilar materials;
an insulating material within which is embedded said conducting member; and
a meter;
wherein the insulating material has one or more gaps located along the insulating material that expose the conducting member without allowing direct contact between the insulating material and the structure or material when the sensor is placed against the structure or material, and the meter is arranged to detect a potential difference between a pair of said conducting elements.

13. A sensor as claimed in claim 12, wherein said meter is arranged to output a signal in response to a predefined value of said potential difference or a predefined change in said potential difference.

14. A sensor as claimed in claim 13, wherein said signal is indicative of said potential difference, is indicative of said change in said potential difference or is an alarm signal.

15. A method for monitoring a structure or material, comprising:
placing a sensor against said structure or material, the sensor comprising a continuous elongate conducting member embedded within an insulating material having one or more gaps located along the insulating material that expose the conducting member without allowing direct contact between the insulating material and the structure or material when the sensor is placed against the structure or material; and
monitoring, with a conductivity or resistance meter, conductivity or resistance between said structure or material and said conducting member, or between two regions of said conducting member.

16. A method as claimed in claim 15, including configuring said meter to issue an alarm or other signal when said conductivity decreases significantly or said resistance increases significantly.

17. A method as claimed in claim 15, including adhering said sensor to said structure or material.

18. A method as claimed in claim 15, including embedding said sensor in a coating applied to said structure or material.

19. A method as claimed in claim 15, including employing time-of-flight measurements or rise time measurements to locate a location of corrosion or deterioration.

20. A method as claimed in claim 15, including employing frequency dependent measurements to measure a complex impedance of said sensor.

21. A method as claimed in claim 15, comprising monitoring, with the meter, conductivity or resistance both between said structure or material and said conducting member and between two regions of said conducting member.

22. A sensor for monitoring a structure or material, comprising:
an elongate conducting member comprising a plurality of conducting elements, each of said conducting elements comprising a wire or metallic ribbon; and
an insulating material within which is embedded said conducting material; and
a meter;
wherein said insulating material has one or more gaps located along said insulating material that expose said conducting member without allowing direct contact between said insulating material and said structure or material when said sensor is placed against said structure or material, each of said gaps comprising an aperture or annular break in said insulating material that is filled with a material or materials sensitive to chemical or physical stimuli so that the sensor is sensitive to the chemical or physical stimuli, and the meter is arranged to monitor either (i) conductivity or resistance between the conducting member and the structure or material or between two regions of the conducting member, or (ii) a potential difference between a pair of the conducting elements.

23. A method of monitoring a structure or material, comprising:
placing a sensor against the structure or material, the sensor comprising an elongate conducting member comprising a plurality of conducting elements of dissimilar materials and embedded within an insulating material having one or more gaps located along the insulating material that expose the conducting member without allowing direct contact between the insulating material and the structure or material when the sensor is placed against the structure or material; and
detecting, with a meter, a potential difference between a pair of the conducting elements.

* * * * *

UNITED STATES PATENT AND TRADEMARK OFFICE
CERTIFICATE OF CORRECTION

| | | |
|---|---|---|
| PATENT NO. | : 8,400,172 B2 | Page 1 of 1 |
| APPLICATION NO. | : 12/863401 | |
| DATED | : March 19, 2013 | |
| INVENTOR(S) | : Alan Richard Wilson | |

It is certified that error appears in the above-identified patent and that said Letters Patent is hereby corrected as shown below:

In the Claims

Claim 1, Column 8, line 58, after "between said", delete "insulating material" and insert -- conducting material --.

Claim 12, Column 9, line 35, after "between the", delete "insulating member" and insert -- conducting member --.

Claim 15, Column 9, line 54, after "between the", delete "insulating member" and insert -- conducting member --.

Claim 22, Column 10, line 34, after "between said", delete "insulating member" and insert -- conducting member --.

Claim 24, Column 10, line 54, after "between the", delete "insulating member" and insert -- conducting member --.

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,400,172 B2 | Page 1 of 1 |
| APPLICATION NO. | : 12/863401 | |
| DATED | : March 19, 2013 | |
| INVENTOR(S) | : Alan Richard Wilson | |

It is certified that error appears in the above-identified patent and that said Letters Patent is hereby corrected as shown below:

In the Specification

Column 1, line 59, after "between the", delete "insulating material" and insert --conducting member--.

Signed and Sealed this
Twenty-first Day of October, 2014

Michelle K. Lee
*Deputy Director of the United States Patent and Trademark Office*